United States Patent [19]

Cavani et al.

[11] Patent Number: 4,992,608
[45] Date of Patent: Feb. 12, 1991

[54] METHOD FOR PREPARING CUMENE

[75] Inventors: Fabrizio Cavani, Modena; Virginio Arrigoni, Milan, both of Italy

[73] Assignees: Enichem Synthesis SpA, Palermo; Eniricerche SpA, Milan, both of Italy

[21] Appl. No.: 342,178

[22] Filed: Apr. 24, 1989

[30] Foreign Application Priority Data

May 6, 1988 [IT] Italy ................................ 20495 A/88

[51] Int. Cl.$^5$ ............................ C07C 2/68; C07C 5/22
[52] U.S. Cl. .................................... 585/467; 585/470; 585/474
[58] Field of Search ....................... 585/468, 470, 474; 502/235

[56] References Cited

U.S. PATENT DOCUMENTS 3,350,469 10/1967 Ryan ..................................... 585/474
3,784,621 1/1974 Suggitt et al. ........................ 585/470
3,786,107 1/1974 Kuribayashi et al. ............... 585/468
4,314,091 2/1982 Crone et al. ......................... 585/474

FOREIGN PATENT DOCUMENTS 507452 11/1954 Canada ................................ 585/468
0160145 6/1985 European Pat. Off. ............ 585/468
512979 5/1955 United Kingdom ................ 585/468

Primary Examiner—Davis: Curtis R.
Attorney, Agent, or Firm—Hedman, Gibson, Costigan & Hoare

[57] ABSTRACT

Cumene is prepared by alkylation of benzene with propylene, or by transalkylation of diisopropylbenzenes in the presence of benzene, on a silica and alumina gel catalyst which is amorphous to X-rays and has an $SiO_2/Al_2O_3$ ratio of between 50/1 and 300/1, a surface area of between 500 and 1000 m$^2$/g, an overall pore volume of between 0.3 and 0.6 ml/g and mean pore diameter of the order of 10 Å, and which is free or substantially free of pores having a diameter exceeding 30 Å.

11 Claims, No Drawings

METHOD FOR PREPARING CUMENE

This invention relates to a method for preparing cumene by the catalytic alkylation of benzene with propylene or by the catalytic transalkylation of diisopropylbenzenes conducted in the presence of benzene.

Processes involving the alkylation of benzene with propylene utilising solid phosphoric acid catalysts are known and are used industrially. These processes suffer substantially from the drawbacks deriving from corrosion problems and from the disposal of the exhausted catalyst.

To obviate these drawbacks, alkylation methods have been proposed in the art using zeolite catalysts, in particular zeolite Y, as described for example in U.S. Pat. Nos. 4,459,425, 4,570,027 and 4,395,372. However these catalysts have a much lower selectivity towards the useful reaction product than conventional catalysts because of the greater formation of polyalkylation products and oligomerization phenomena exercised on the alkylating agent.

Published European patent application No. 160,145 describes a method for the alkylation of aromatic hydrocarbons which uses an amorphous silica and alumina gel catalyst having a pore diameter typically of the order of 50-500 Å and with a silica to alumina ratio typically of between 1/1 and 10/1. These catalysts show good activity in relation to those alkylating agents containing between 4 and 20 carbon atoms per molecule.

It has now been found possible to obtain cumene by alkylation of benzene with propylene with an unexpectedly high selectivity towards the useful reaction product, by operating in the presence of a catalyst consisting of a particular amorphous silica and alumina gel of high surface area which is microporous and has a restricted pore distribution. It has also been found that such a catalyst is active in the transalkylation of diisopropylbenzenes conducted in the presence of benzene.

In accordance therewith the present invention provides a process for producing cumene by the alkylation of benzene with propylene, or by the transalkylation of diisopropylbenzenes in the presence of benzene, characterised by using as alkylation or transalkylation catalyst a silica and alumina gel which is amorphous to X-rays and has an $SiO_2/Al_2O_3$ ratio of between 50/1 and 300/1, a surface area of between 500 and 1000 m$^2$/g, an overall pore volume of between 0.3 and 0.6 ml/g and a mean pore diameter of the order of 10 Å, and which is free or substantially free of pores having a diameter exceeding 30 Å.

Such a silica and alumina gel can be obtained by:

(a) preparing an aqueous solution containing tetra alkyl ammonium hydroxide (TAA-OH) in which the alkyl is chosen from ethyl, n-propyl and n-butyl, a soluble aluminum compound able to hydrolyze in $Al_2O_3$ and a soluble silicon compound able to hydrolyze in $SiO_2$, the quantity of the solution constituents being such as to respect the following molar ratios:

| | |
|---|---|
| $SiO_2/Al_2O_3$ | from 30/1 to 500/1 |
| TAA—OH/$SiO_2$ | from 0.05/1 to 0.2/1 |
| $H_2O/SiO_2$ | from 5/1 to 40/1; |

(b) heating the obtained mixture to cause gelling;
(c) drying the gel obtained;
(d) calcining the dried gel operating firstly in an inert atmosphere and then in an oxidising atmosphere.

The aluminium trialkoxide used in stage a) is preferably aluminium tri-n-propoxide or aluminium tri isopropoxide. The tetraalkylsilicate used in stage a) is prefereably tetraethylsilicate. Stage (a) is conveniently conducted at ambient temperature (20°-25° C.).

The following molar ratios are preferably respected in stage (a):

| | |
|---|---|
| $SiO_2/Al_2O_3$ | from 50/1 to 300/1 |
| TAA—OH/$SiO_2$ | from 0.05/1 to 0.2/1 |
| $H_2O/SiO_2$ | from 10/1 to 25/1. |

Stage (b) is conducted at a temperature of the order of 50°-70° C. and preferably about 60° C. The drying in stage (c) is conducted at a temperature of up to 150° C. It can be convenient to initiate stage (c) by spray-drying.

The calcining of stage (d) is conveniently conducted at a temperature in the range of 500° to 700° C. and preferably about 550°-600° C., operating firstly in a nitrogen environment and then in the presence of air.

The silica and alumina gel thus obtained, having the aforesaid general characteristics, is greatly active in the alkylation of aromatic hydrocarbons with olefins or relative precursors, and furthermore it is particularly selective in the alkylation of benzene with propylene.

Consequently such silica and alumina gel has the inherent advantages of zeolite Y such as the high activity and compared with these is more selective towards the monoalkylation product cumene (isopropylbenzene) for equal reactant ratios.

The silica and alumina gel used as catalyst can be mixed with suitable metal oxides acting as binders. Suitable oxides for this purpose are aluminas, silicas, or titanium, magnesium or zirconium oxides. The silica and alumina gel and the binder can be mixed in weight ratios of between 50/50 and 95/5, and preferably between 70/30 and 90/10. The two components can be mixed by conventional methods and the mixture is conveniently consolidated into the final desired form, such as extrusions or granules. By operating in this manner the catalyst can be given improved mechanical properties.

The alkylation reaction can be conducted batchwise, semicontinuously or preferably continuously. The reaction is preferably carried out continuously in a flow reactor at a temperature of between 100° and 250° C., preferably between 110° and 200° C., at a pressure of between 20 and 50 ata, preferably of the order of 30 ata, and with the reactants (benzene and propylene) being fed at a WHSV of between 0.1 and 50 hour$^{-1}$.

The reaction can be conducted in the gaseous phase, however it is preferable to operate in the liquid or mixed (liquid-vapour) phase. This minimizes carbon formation, so extending the catalyst life and giving improved selectivity.

The molar feed ratio of benzene to propylene can generally vary from 2/1 to 30/1 but it is preferable to operate within the range of 4/1 to 15/1. Within this range the catalyst life (time before regeneration) can be kept long, and the formation of higher molecular weight compounds (polyalkylates and propylene oligomers) can be minimized.

The alkylation reaction is exothermic and therefore under industrial conditions the temperature is controlled preferably by feeding cold benzene or inert paraffins (such as propane) at various levels of the catalyst bed.

The described silica and alumina gel is also active in the transalkylation of diisopropylbenzenes in the presence of benzene. These diisopropylbenzenes can be the by-products of the alkylation of benzene with propylene. The molar ratio of benzene to diisopropylbenzenes can conveniently vary from 10/1 to 40/1 and the transalkylation reaction can be conducted at a temperature of between 150° and 250° C. at a pressure of between 10 and 40 ata and, in the case of a continuous process, with a reactant feed rate in terms of WHSV of between 1 and 30 hour$^{-1}$. The transalkylation reaction can be conveniently conducted in the liquid phase. In the experimental examples given hereinafter a silica and alumina gel is used having the following characteristics:

amorphous to X-rays (analysis conducted on powder by Philips vertical goniometer using Cu K $\alpha$ radiation);

| molar SiO$_2$/Al$_2$O$_3$ ratio | 100/1 |
| --- | --- | surface area = 800 m$^2$/g (measured by Carlo Erba Sorptomatic 1800 apparatus);
porosity = 0.44 ml/g, mean pore diameter about 10 Å, absence of pores with diameter exceeding 30 Å (values determined by Carlo Erba Sorptomatic 1800 apparatus).

This silica and alumina gel was prepared by the following procedure.

2.0 g of aluminium tri isopropylate are dissolved in 34 g of 30.6 weight% tetrapropyl ammonium hydroxide (TPA-OH), and 162 g of demineralized water are added.

These operations are conducted at ambient temperature (about 20° C.).

The solution obtained is heated to 60° C. and 104 g of tetraethyl silicate (TES) are added while stirring. The mixture obtained has the following molar ratios:

| SiO$_2$/Al$_2$O$_3$ | 100/1 |
| --- | --- |
| TAA-OH/SiO$_2$ | 0.10/1 |
| H$_2$O/SiO$_2$ | 21/1. |

The mixture is kept stirring at 60° C. and after 30 minutes a homogeneous gel is obtained and dried in a Rotavapor flask in an air stream with a bath temperature-controlled at 90° C., followed by drying in an oven at 100° C.

The dried gel is calcined at 550° C. for 3 hours in a nitrogen stream and then for 10 hours in an air stream.

In this manner 30 g of silica and alumina gel are obtained with quantitative yield with respect to the initially fed silicon and aluminium, and having the said characteristics.

The experimental examples given hereinafter further illustrate the invention.

In these examples alkylation tests on benzene with propylene and transalkylation tests on diisopropylbenzenes in the presence of benzene are described using the aforesaid silica and alumina gel catalyst.

For comparison purposes alkylation tests on benzene with propylene are described using zeolite Y of the known art.

EXAMPLE 1

20.0 g of silica and alumina gel having the characteristics given in the description are fed into an autoclave together with 300 ml of benzene and 9.8 g of propylene. The molor ratio of feed benzene to propylene is therefore 14.5/1.

The autoclave is pressurised with nitrogen to obtain a total pressure of 40 ata at the reaction temperature, which is fixed at 160° C. The mass is kept stirred for one hour after which the reactor contents are discharged and analysed chromatographically by means of a Hewlett Packard gas chromatograph with an OV 101 wide bore column and an 80°–240° C. programmed temperature.

The results of this analysis are given in Table 1, in which the headings have the following meanings:
C$_6$ % conv. = percentage conversion of benzene
C$_3$ % conv. = percentage conversion of propylene
C$_6$ % sel. = molar percentage selectivity of benzene converted into cumene
C$_3$ % sel. = molar percentage selectivity of propylene converted into cumene.

EXAMPLE 2

Comparison

Example 1 is repeated using as catalyst a protonic zeolite Y produced commercially by Union Carbide (Linde LZ-Y 62; 1/16" extrusions). The results of this test are given in Table 1.

EXAMPLE 3

The procedure of Example 1 is followed using the same silica and alumina gel catalyst, but with the following conditions: temperature 150° C., pressure 30 ata, molar ratio of feed benzene to propylene 8.0/1 (300 ml benzene fed) and reaction time 1.5 hours. The results of this test are given in Table 1.

EXAMPLE 4

Comparison

The procedure of Example 3 is followed using as catalyst a commercial zeolite Y of Toyo Soda (TSZ 360 HUD, in extrusion form). The results of this test are given in Table 1.

EXAMPLE 5

The procedure of Example 1 is followed using the same silica and alumina gel catalyst, but with the following conditions: temperature 150° C., pressure 10.5 ata (autogenous system pressure at the stated temperature), molar ratio of feed benzene to propylene 8.0/1 and reaction time 2 hours. The results of this test are given in Table 1.

EXAMPLE 6

Comparison

The procedure of Example 5 is followed using the zeolite Y of Example 2 as catalyst. The results are given in Table 1.

EXAMPLE 7

Comparison

The procedure of Example 5 is followed using the zeolite Y of Example 4. The results are given in Table 1.

TABLE 1

| EXAMPLE | $C_6$ % CONV. | $C_2$ % CONV. | $C_6$ % SEL. | $C_3$ % SEL. |
|---|---|---|---|---|
| 1 | 4.8 | 72.1 | 95.7 | 91.7 |
| 2 | 5.3 | 85.2 | 93.2 | 87.2 |
| 3 | 8.5 | 73.8 | 91.3 | 83.4 |
| 4 | 9.0 | 82.2 | 88.3 | 78.7 |
| 5 | 8.3 | 70.4 | 92.7 | 86.3 |
| 6 | 8.1 | 71.6 | 90.0 | 81.4 |
| 7 | 8.0 | 71.5 | 89.3 | 80.3 |

Besides a high activity, better selectivity will be noted in the case of the examples conducted according to the invention than in those conducted with zeolite Y catalysts.

These better selectivity values derive from the smaller quantity of diisopropylbenzene by-products and the absence or virtual absence of butylbenzenes and pentylbenzenes. The diisopropylbenzenes form by consecutive alkylation reactions between benzene and propylene.

The butylbenzens and pentylbenzenes present as by-products in the examples conducted using zeolite Y as catalyst presumably form following oligomerization of the propylene to nonene, cracking of said nonene to $C_5$ and $C_4$ olefins and benzene alkylation by these olefins.

EXAMPLE 8

The autoclave of Example 1 is used for a transalkylation test using silica and alumina gel with the characteristics given in the description. Specifically, 20 g of said catalyst are used, feeding into the reactor 256 g of benzene and 17 g of diisopropylbenzenes (molar ratio of the two reactants 31/1). The reaction conditions are: pressure 30 ata, temperature 250° C., reaction time 2 hours.

Analysis of the reaction products indicates a diisopropylbenzene conversion of 86% with a selectivity towards cumene of 90%.

EXAMPLE 9

The procedure of Example 8 is repeated except that the reaction temperature is fixed at 210° C. In this case the diisopropylbenzene conversion is 76% with a cumene selectivity of 90%.

EXAMPLE 10

The alkylation reaction in the presence of silica and alumina gel having the characteristics given in the description is conducted in a vertical flow reactor. The reactor is formed from a 36 mm diameter tube of height 900 mm. A multiple thermocouple is inserted longitudinally to measure the catalyst bed temperature at various levels. The reactor is immersed in a bath of fluidized alumina to remove the heat of reaction.

In this example the silica and alumina gel catalyst is mixed with γ-alumina in a weight ratio of 100:25 and formed into ⅛" diameter extrusions of average length 8 mm. The reaction conditions are:

temperature 160° C., pressure 40 ata, molar ratio of feed benzene to propylene 14.5/1, feed rate of organic phase (benzene+propylene) in WHSV 9.1 hour$^{-1}$. The operation proceeds continuously for about 300 hours without observing appreciable variations in the catalyst behaviour. Reactant conversions and selectivity towards the useful reaction product are totally similar to those of Example 1.

We claim:

1. A process for preparing cumene by the alkylation reaction of benzene with propylene, comprising conducting the reaction in the presence of an alkylation catalyst comprising a silica and alumina gel, said catalyst being amorphous to X-rays and having a $SiO_2/Al_2O_3$ ratio of from 50/1 to 300/1, a surface area of from 500 to 1000 m$^2$/g, an overall pore volume of from 0.3 to 0.6 ml/g and a mean pore diameter of about 10 Angstroms, said catalyst being at least substantially free of pores having a diameter exceeding 30 Angstroms.

2. A process as defined in claim 1, wherein said silica and alumina gel is prepared by a process comprising:
   (a) preparing an aqueous solution consisting essentially of tetra alkyl ammonium hydroxide (TAA-OH) wherein the alkyl is selected from the group consisting of ethyl, n-propyl, n-butyl, and mixtures of the foregoing; a soluble aluminum compound able to hydrolyze to $Al_2O_3$; and a soluble silicon compound able to hydrolyze to $SiO_2$, wherein said aqueous solution comprises the following molar ratios:
   $SiO_2/Al_2O_3$ from 30/1 to 500/1
   TAA-OH/$SiO_2$ from 0.05/1 to 0.2/1
   $H_2O/SiO_2$ from 5/1 to 40/1;
   (b) heating the solution to produce a gel;
   (c) drying the gel; and
   (d) calcining the dried gel in an inert atmosphere and then in an oxidizing atmosphere.

3. A process as defined in claim 2, wherein said soluble aluminum compound is selected from aluminum tri-n-propoxide and aluminum tri iso-propoxide and the soluble silicon compound is tetraethylsilicate; wherein the step of heating the gel is performed at a temperature of from 50° to 70° C.; the drying step is performed at a temperature not exceeding about 150° C.; and the calcining step is performed at a temperature of from 500° to 700° C.

4. A process as defined in claim 2, wherein said aqueous solution comprises the following molar ratios:
   $SiO_2/Al_2O_3$ from 50/1 to 300/1
   TAA-OH/$SiO_2$ from 0.05/1 to 0.2/1
   $H_2O/SiO_2$ from 10/1 to 25/1.

5. A process as defined in claim 1, wherein said reaction is conducted at a temperature of from 100° to 250° C. and a pressure of from 20 to 50 atmospheres absolute, and wherein benzene and propylene are present in a molar ratio of from 2/1 to 30/1.

6. A process as defined in claim 1, wherein said reaction is conducted at a temperature of from 110° to 200° C. and a pressure of about 30 atmospheres absolute and wherein the benzene to propylene molar ratio is from 4/1 to 15/1.

7. A process for preparing cumene by the transalkylation reaction of benzene with diisopropylbenzene, comprising conducting the reaction in the presence of a transalkylation catalyst comprising a silica and alumina gel, said catalyst being amorphous to X-rays and having a $SiO_2/Al_2O_3$ ratio of from 50/1 to 300/1, a surface area of from 500 to 1000 m$^2$/g, an overall pore volume of from 0.3 to 0.6 ml/g and a mean pore diameter of about 10 Angstroms, said catalyst being at least substantially free of pores having a diameter exceeding 30 Angstroms.

8. A process as defined in claim 7, wherein said silica and alumina gel is prepared by a process comprising:
   (a) preparing an aqueous solution consisting essentially of tetra alkyl ammonium hydroxide (TAA-OH) wherein the alkyl is selected from the group consisting of ethyl, n-propyl, n-butyl and mixtures of the foregoing; a soluble aluminum compound able to hydrolyze to $Al_2O_3$; and a soluble silicon compound able to hydrolyze to $SiO_2$, wherein said aqueous solution comprises the following molar ratios:

$SiO_2/Al_2O_3$ from 30/1 to 500/1
TAA-OH/$SiO_2$ from 0.05/1 to 0.2/1
$H_2O/SiO_2$ from 5/1 to 40/1.

(b) heating the solution to produce a gel;
(c) drying the gel; and
(d) calcining the dried gel in an inert atmosphere and then in an oxidizing atmosphere.

9. A process as defined in claim 8, wherein said soluble aluminum compound is selected from aluminum tri-n-propoxide and aluminum tri iso-propoxide and the soluble silicon compound is tetraethylsilicate; wherein the step of heating the gel is performed at temperature of from 50° to 70° C.; the drying step is performed at a temperature not exceeding about 150° C.; and the calcining step is performed at a temperature of from 500° to 700° C.

10. A process as defined in claim 8, wherein said aqueous solution comprises the following molar ratios:

$SiO_2/Al_2O_3$ from 50/1 to 300/1
TAA-OH/$SiO_2$ from 0.05/1 to 0.2/1
$H_2O/SiO_2$ from 10/1 to 25/1.

11. A process as defined in claim 7, wherein said reaction is conducted at a temperature of from 150° to 250° C. and a pressure of from 10 to 40 atmospheres absolute and wherein benzene and diisopropylbenzene are present in a molar ratio of from 10/1 to 40/1.

* * * * *

UNITED STATES PATENT AND TRADEMARK OFFICE
CERTIFICATE OF CORRECTION

PATENT NO. : 4,992,608
DATED : February 12, 1991
INVENTOR(S) : Fabrizio Cavani et al.

It is certified that error appears in the above-identified patent and that said Letters Patent is hereby corrected as shown below:

Title Page:

Item [75]  after "Virginio Arrigoni, Milan," insert -- Giuseppe Bellussi, Piacenza, -- and delete "both of" insert -- all of --.

Signed and Sealed this

Sixth Day of July, 1993

Attest:

MICHAEL K. KIRK

*Attesting Officer*       *Acting Commissioner of Patents and Trademarks*